US006328718B1

(12) United States Patent
Chiang et al.

(10) Patent No.: US 6,328,718 B1
(45) Date of Patent: Dec. 11, 2001

(54) SNIVEL SUCKER

(75) Inventors: Alex Chiang, Da Li; Chein-Li Chen, Taichung, both of (TW)

(73) Assignee: Chien-Li Chen, Taichung Shies (TW)

( * ) Notice: Subject to any disclaimer, the term of this patent is extended or adjusted under 35 U.S.C. 154(b) by 0 days.

(21) Appl. No.: 09/561,765

(22) Filed: Apr. 29, 2000

(51) Int. Cl.$^7$ .................................................. A61M 1/00
(52) U.S. Cl. ..................... 604/319; 604/320; 604/321; 604/322; 604/323; 604/324; 604/325; 604/326; 604/902
(58) Field of Search ................... 604/319–326, 604/902

(56) References Cited

U.S. PATENT DOCUMENTS

| | | | | |
|---|---|---|---|---|
| 4,947,841 | * | 8/1990 | Ng | 128/207.14 |
| 5,114,415 | * | 5/1992 | Shedlock | 604/319 |
| 5,458,138 | * | 10/1995 | Gajo | 128/125.24 |
| 5,788,683 | * | 8/1998 | Martin | 604/319 |

FOREIGN PATENT DOCUMENTS

| | | | | |
|---|---|---|---|---|
| 38 05 609 A1 | * | 9/1989 | (DE) | A61M/1/00 |
| 2 582 519 A1 | * | 12/1986 | (FR) | A61M/1/00 |
| 2 234 902 A | * | 2/1991 | (GB) | A61M/1/00 |

* cited by examiner

*Primary Examiner*—John G. Weiss
*Assistant Examiner*—Michael Bogart
(74) *Attorney, Agent, or Firm*—Alan Kamrath; Rider, Bennett, Egan & Arundel, LLP

(57) ABSTRACT

A snivel sucker has a hollow main body, a lower cover disposed on a bottom of the hollow main body, a battery disposed in the hollow main body, a male top casing disposed on a top portion of the hollow main body, a female top casing disposed on the top portion of the hollow main body, the male top casing engaging with the female top casing, and a collector device disposed on a front portion of the male top casing. A motor receiving seat, a rubber cushion, a positioning seat, a rubber plate, and a connection mount are disposed between the male top casing and the female top casing. A motor is disposed in the motor receiving seat.

3 Claims, 5 Drawing Sheets

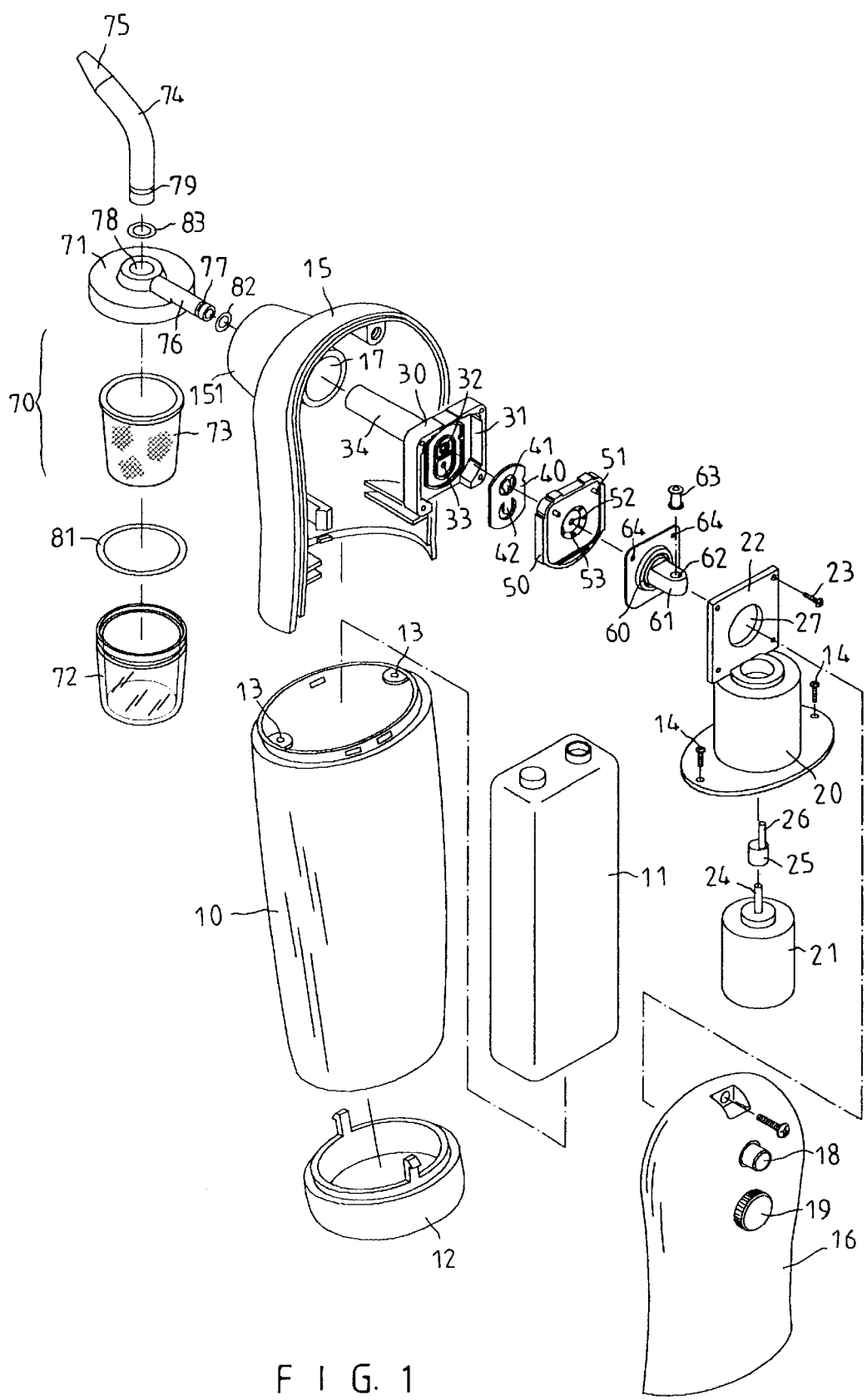
F I G. 1

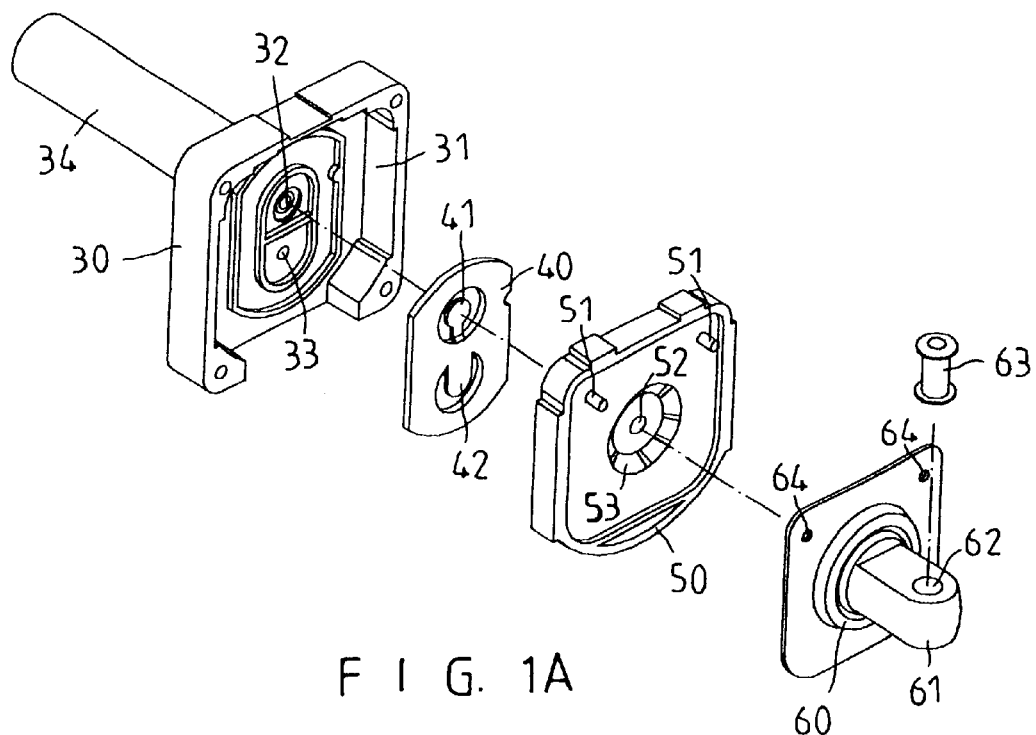
F I G. 1A
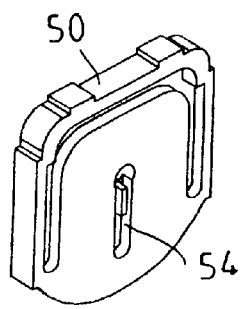
F I G. 1B

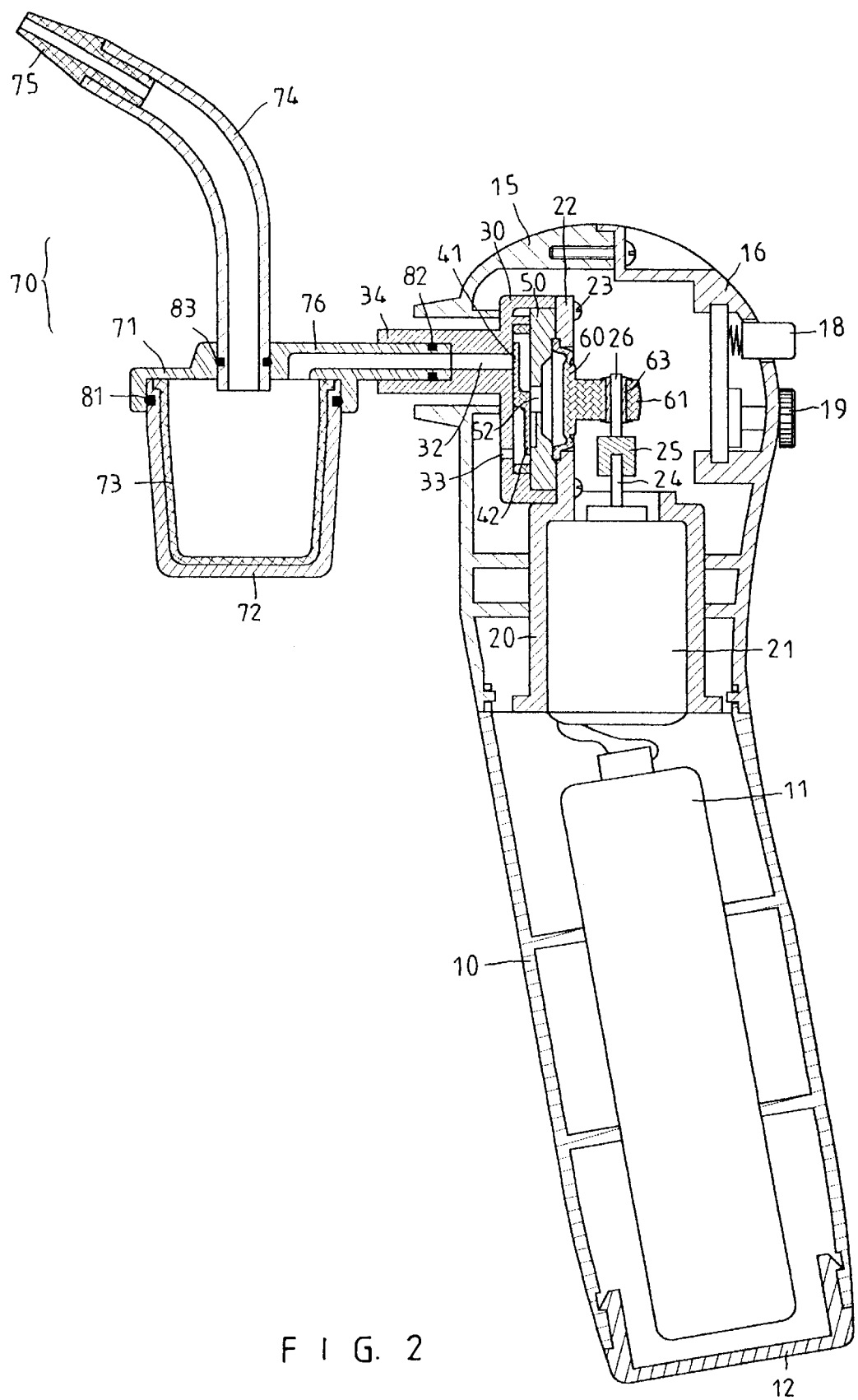
F I G. 2

SNIVEL SUCKER

BACKGROUND OF THE INVENTION

The present invention relates to a snivel sucker. More particularly, the present invention relates to a snivel sucker which is operated electrically.

A conventional snivel sucker has a tube and a ball connected to the tube. However, the conventional snivel sucker should be operated manually.

SUMMARY OF THE INVENTION

An object of the present invention is to provide a snivel sucker which can be operated easily.

Accordingly, a snivel sucker comprises a hollow main body, a lower cover disposed on a bottom of the hollow main body, a battery disposed in the hollow main body, a male top casing disposed on a top portion of the hollow main body, a female top casing disposed on the top portion of the hollow main body, the male top casing engaging with the female top casing, and a collector device disposed on a front portion of the male top casing. The hollow main body has two upper inner lugs. A hollow motor receiving seat, a rubber cushion, a positioning seat, a rubber plate, and a connection mount are disposed between the male top casing and the female top casing. A motor is disposed in the hollow motor receiving seat. The battery provides electricity for the motor. The motor has a motor shaft. A rotor has an eccentric shaft. The motor shaft is inserted in the rotor. An upper panel is disposed on a top portion of the hollow motor receiving seat. The upper panel has a center hole. The hollow motor receiving seat is disposed on the upper inner lugs. Two screws fasten the hollow motor receiving seat and the upper inner lugs together. The male top casing has a barrel. The barrel has a through hole. The connection mount has an interior, an inhale pipe, an outlet vent, and an inlet vent communicating with the inhale pipe. The interior of the connection mount receives the rubber plate, the positioning seat, and the rubber cushion. The rubber plate has an upper diaphragm and a lower diaphragm. The upper diaphragm matches the inlet vent. The lower diaphragm matches the outlet vent. The positioning seat has two posts, an air chamber, a center aperture communicating with the air chamber, and an exhale hole communicating with the center aperture. The rubber cushion has two positioning apertures. A pillar is disposed on a center of the rubber cushion. The pillar has a through aperture. A shaft sleeve is inserted in the through aperture of the pillar. Two bolts fasten the upper panel and the connection mount together. The pillar passes through the center hole of the upper panel. The eccentric shaft is inserted in the shaft sleeve. The inhale pipe is inserted through the barrel via the through hole of the barrel. The collector device has a cup, a first O-ring enclosing an upper periphery of the cup, a cup-shaped lining disposed in the cup, and an upper cover covering the cup. The upper cover has a round hole and an insertion tube. The insertion tube is inserted in the inhale pipe. The insertion tube has an annular groove. A second O-ring encloses the annular groove of the insertion tube. A guide tube is inserted in the round hole of the upper cover. The guide tube has a distal end and an annular recess. A third O-ring encloses the annular recess of the guide tube.

BRIEF DESCRIPTION OF THE DRAWINGS

FIG. 1 is a perspective exploded view of a snivel sucker of a preferred embodiment in accordance with the present invention;

FIG. 1A is a perspective exploded view of a rubber cushion, a positioning seat, a rubber plate, and a connection mount of a preferred embodiment in accordance with the present invention;

FIG. 1B is a perspective view of a positioning seat of a preferred embodiment in accordance with the present invention;

FIG. 2 is a sectional assembly view of a snivel sucker of a preferred embodiment in accordance with the present invention;

DETAILED DESCRIPTION OF THE INVENTION

Figure 3:
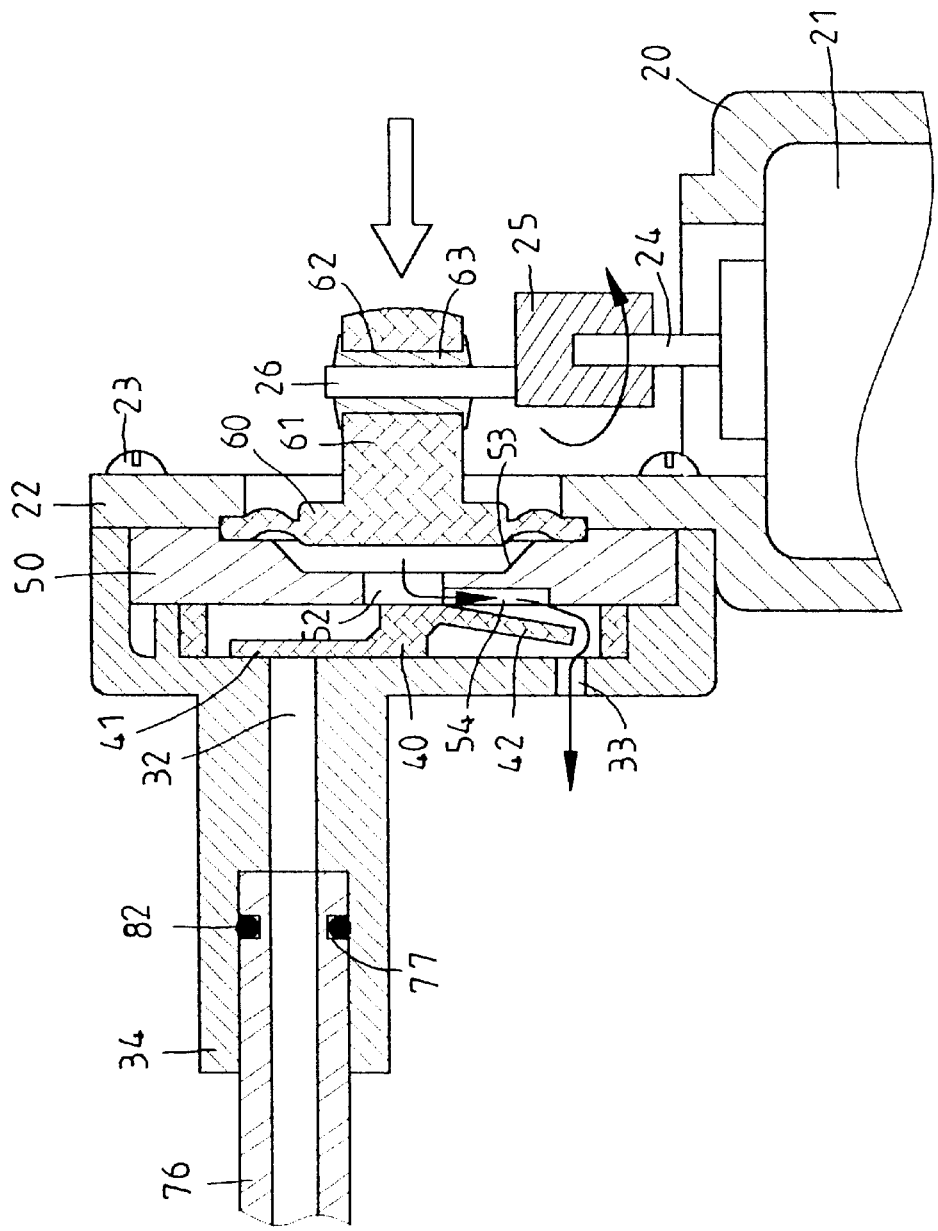
FIG. 3 is a schematic view illustrating an inhaling operation of a snivel sucker of a preferred embodiment in accordance with the present invention.
Figure 4:
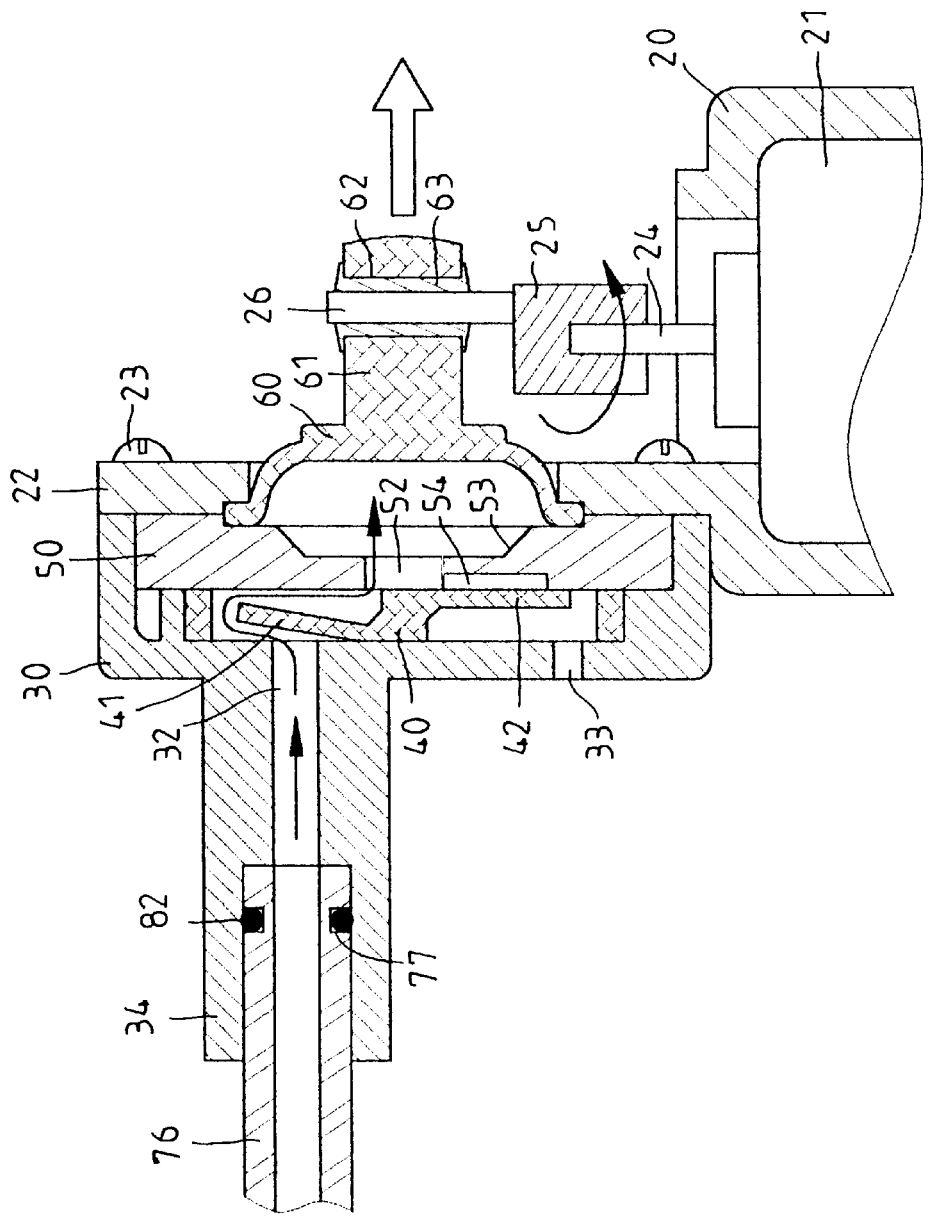
FIG. 4 is a schematic view illustrating an exhaling operation of a snivel sucker of a preferred embodiment in accordance with the present invention.

Referring to FIGS. 1 to 4, a snivel sucker comprises a hollow main body 10, a lower cover 12 disposed on a bottom of the hollow main body 10, a battery 11 disposed in the hollow main body 10, a male top casing 15 disposed on a top portion of the hollow main body 10, a female top casing 16 disposed on the top portion of the hollow main body 10, the male top casing 15 engaging with the female top casing 16, and a collector device 70 disposed on a front portion of the male top casing 15.

The hollow main body 10 has two upper inner lugs 13.

A hollow motor receiving seat 20, a rubber cushion 60, a positioning seat 50, a rubber plate 40, and a connection mount 30 are disposed between the male top casing 15 and the female top casing 16.

A motor 21 is disposed in the hollow motor receiving seat 20. The battery 11 provides electricity for the motor 21. The motor 21 has a motor shaft 24.

A rotor 25 has an eccentric shaft 26. The motor shaft 24 is inserted in the rotor 25.

An upper panel 22 is disposed on a top portion of the hollow motor receiving seat 20. The upper panel 22 has a center hole 27.

The hollow motor receiving seat 20 is disposed on the upper inner lugs 13. Two screws 14 fasten the hollow motor receiving seat 20 and the upper inner lugs 13 together.

The male top casing 15 has a barrel 151. The barrel 151 has a through hole 17.

The connection mount 30 has an interior 31, an inhale pipe 34, an outlet vent 33, and an inlet vent 32 communicating with the inhale pipe 34.

The interior 31 of the connection mount 30 receives the rubber plate 40, the positioning seat 50, and the rubber cushion 60.

The rubber plate 40 has an upper diaphragm 41 and a lower diaphragm 42. The upper diaphragm 41 matches the inlet vent 32. The lower diaphragm 42 matches the outlet vent 33.

The positioning seat 50 has two posts 51, an air chamber 53, a center aperture 52 communicating with the air chamber 53, and an exhale hole 54 communicating with the center aperture 52.

The rubber cushion 60 has two positioning apertures 64. A pillar 61 is disposed on a center of the rubber cushion 60. The pillar 61 has a through aperture 62.

A shaft sleeve 63 is inserted in the through aperture 62 of the pillar 61.

Two bolts 23 fasten the upper panel 22 and the connection mount 30 together.

The pillar 61 passes through the center hole 27 of the upper panel 22.

The eccentric shaft 26 is inserted in the shaft sleeve 63.

The inhale pipe 34 is inserted through the barrel 151 via the through hole 17 of the barrel 151.

The collector device 70 has a cup 72, a first O-ring 81 enclosing an upper periphery of the cup 72, a cup-shaped lining 73 disposed in the cup 72, and an upper cover 71 covering the cup 72.

The upper cover 71 has a round hole 78 and an insertion tube 76. The insertion tube 76 is inserted in the inhale pipe 34.

The insertion tube 76 has an annular groove 77. A second O-ring 82 encloses the annular groove 77 of the insertion tube 76.

A guide tube 74 is inserted in the round hole 78 of the upper cover 71. The guide tube 74 has a distal end 75 and an annular recess 79. A third O-ring 82 encloses the annular recess 79 of the guide tube 74.

The cup-shaped lining 73 is made of a non-woven fabric.

A switch 18 and an adjustment button 19 are disposed on the female top casing 16.

Referring to FIG. 3 again, the upper diaphragm 41 will open while the rubber cushion 60 expands and an air is inhaled via the inhale pipe 34. Then the lower diaphragm 42 will be closed.

Referring to FIG. 4 again, the lower diaphragm 42 will open and the upper diaphragm 41 will be closed while the rubber cushion 60 compresses.

When the eccentric shaft 26 drives the pillar 61 to move rearward, the rubber cushion 60 expands.

When the eccentric shaft 26 drives the pillar 61 to move forward, the rubber cushion 60 compresses.

The invention is not limited to the above embodiment but various modification thereof may be made. Further, various changes in form and detail may be made without departing from the scope of the invention.

What is claimed is:

1. A snivel sucker comprising:
   a hollow main body, a lower cover disposed on a bottom of the hollow main body, a battery disposed in the hollow main body, a male top casing disposed on a top portion of the hollow main body, a female top casing disposed on the top portion of the hollow main body, the male top casing engaging with the female top casing, and a collector device disposed on a front portion of the male top casing,
   the hollow main body having two upper inner lugs,
   a hollow motor receiving seat, a rubber cushion, a positioning seat, a rubber plate, and a connection mount disposed between the male top casing and the female top casing,
   a motor disposed in the hollow motor receiving seat,
   the battery providing electricity for the motor,
   the motor having a motor shaft,
   a rotor having an eccentric shaft,
   the motor shaft inserted in the rotor,
   an upper panel disposed on a top portion of the hollow motor receiving seat,
   the upper panel having a center hole,
   the hollow motor receiving seat disposed on the upper inner lugs,
   two screws fastening the hollow motor receiving seat and the upper inner lugs together,
   the male top casing having a barrel,
   the barrel having a through hole,
   the connection mount having an interior, an inhale pipe, an outlet vent, and an inlet vent communicating with the inhale pipe,
   the interior of the connection mount receiving the rubber plate, the positioning seat, and the rubber cushion,
   the rubber plate having an upper diaphragm and a lower diaphragm,
   the upper diaphragm matching the inlet vent,
   the lower diaphragm matching the outlet vent,
   the positioning seat having two posts, an air chamber, a center aperture communicating with the air chamber, and an exhale hole communicating with the center aperture,
   the rubber cushion having two positioning apertures,
   a pillar disposed on a center of the rubber cushion,
   the pillar having a through aperture,
   a shaft sleeve inserted in the through aperture of the pillar,
   two bolts fastening the upper panel and the connection mount together,
   the pillar passing through the center hole of the upper panel,
   the eccentric shaft inserted in the shaft sleeve,
   the inhale pipe inserted through the barrel via the through hole of the barrel,
   the collector device having a cup, a first O-ring enclosing an upper periphery of the cup, a cup-shaped lining disposed in the cup, and an upper cover covering the cup,
   the upper cover having a round hole and an insertion tube,
   the insertion tube inserted in the inhale pipe,
   the insertion tube having an annular groove,
   a second O-ring enclosing the annular groove of the insertion tube,
   a guide tube inserted in the round hole of the upper cover,
   the guide tube having a distal end and an annular recess, and
   a third O-ring enclosing the annular recess of the guide tube.

2. The snivel sucker as claimed in claim 1, wherein the cup-shaped lining is made of a non-woven fabric.

3. The snivel sucker as claimed in claim 1, wherein a switch and an adjustment button are disposed on the female top casing.

* * * * *